United States Patent [19]

Nagashima et al.

[11] 4,232,685
[45] Nov. 11, 1980

[54] LARYNX STROBOSCOPE FOR PHOTOGRAPHY

[75] Inventors: Hironobu Nagashima, Tokyo; Koji Tuda; Masatoshi Marui, both of Kami Fukuoka, all of Japan

[73] Assignee: Asahi Kogaku Kogyo Kabushiki Kaisha, Tokyo, Japan

[21] Appl. No.: 960,543

[22] Filed: Nov. 14, 1978

[30] Foreign Application Priority Data

Nov. 14, 1977 [JP] Japan .................. 52-136435

[51] Int. Cl.³ .......................... A61B 1/04; A61B 1/06
[52] U.S. Cl. ...................................... 128/773; 354/62
[58] Field of Search ................... 128/630, 665, 773, 6, 128/8; 179/1 AL, 1 SP, 1 SC; 354/62, 63

[56] References Cited

U.S. PATENT DOCUMENTS

| | | | |
|---|---|---|---|
| 3,024,783 | 9/1979 | Timcke | 128/773 |
| 3,318,216 | 5/1967 | Hajjar et al. | 354/62 |
| 3,837,332 | 9/1974 | Meyers | 128/773 |
| 4,086,583 | 4/1978 | Takahashi | 354/62 |
| 4,104,625 | 8/1978 | Bristow et al. | 179/1 SP X |
| 4,153,356 | 5/1979 | Hama | 354/62 |

Primary Examiner—Robert W. Michell
Assistant Examiner—Jeffrey W. Tayon
Attorney, Agent, or Firm—Sughrue, Rothwell, Mion, Zinn and Macpeak

[57] ABSTRACT

A larynx stroboscope device capable of photography following the anode or cathode terminal of a flash discharge tube is connected to a photographing charge-discharge capacitor by the release operation of a camera. A trigger pulse is applied to the trigger terminal of the flash discharge tube in synchronization with a vocal cord vibration signal so that the flash discharge tube emits light while the shutter of said camera is open. Upon completion of a photographing operation, all the functions are automatically restored to the states obtained before the release operation. Alternatively, a charge-discharge system may be used. By the release operation of a camera supply of charging current to said capacitor is suspended. Thereafter a trigger pulse is applied to the trigger terminal of said flash discharge tube in synchronization with a vocal cord vibration frequency so that said flash discharge tube emits light while the shutter of said camera is open.

11 Claims, 4 Drawing Figures

LARYNX STROBOSCOPE FOR PHOTOGRAPHY

BACKGROUND OF THE INVENTION

A larynx stroboscope is a device in which the flash discharge tube emits light by a trigger signal synchronous with a vocal cord vibration so that the vocal cords being vibrated can be observed as if they were at rest or moving at slow speed. The larynx stroboscope is most effective in diagnosing whether or not vocal cords are diseased or whether or not the motion of vocal cords is normal.

There has been a strong demand, in the field of modern diagnostic medicine, to provide a technique in which vocal cords are photographed while the vibration of the vocal cords is being observed. Such a photograph will provide a clear image of the vocal cords. However, in a conventional larynx stroboscope the observing light source and the photographing light source are provided separately. Hence, the operation of the conventional larynx stroboscope is rather difficult and not practical to use. Furthermore, with the conventional larynx stroboscope, when the observing flash light is used for photographing the vocal cords, the intensity of light thereof is generally inadequate, and accordingly it is necessary to carry out multiple exposure photography.

In general, the number of light emissions of the flash discharge tube effectuated while the shutter of a photographing camera is open depends on the number of vibrations of the vocal cords, and therefore it is necessary to change the exposure conditions of the camera in order to obtain a suitable exposure. In addition, if the synchronization of the vocal cords is changed even slightly, it is impossible to obtain a clear image of the vocal cords because of a multiple exposure resulting in a blurred image. Because of the above-described reasons, heretofore, it has been very difficult to obtain a clear image of vocal cords.

SUMMARY OF THE INVENTION

In view of the above-described drawbacks accompanying a conventional larynx stroboscope, according to this invention, a novel larynx stroboscope device capable of photographing vocal cords has been provided. In the larynx stroboscope according to the invention, the timing of the observing light emission and the timing of the photographing light emission are controlled so that the same light source can be used for observing and photographing vocal cords. This eliminates troublesome control and handling. Furthermore, the real time observation light emission is suspended by the release operation of the camera shutter to increase the input power to the flash discharge tube thereby to carry out the photographing operation with a flash light of high intensity. Thereafter the photographing light emission is automatically restored to the observing light emission. Thus, an important aspect of the invention resides in the fact that a clear photographing image of vocal cords can be obtained readily at a desired time instant while the vocal cords being observed and thereafter the photographing state is automatically restored to the observing state.

Accordingly, it is an object of this invention to provide a larynx stroboscope wherein the same light source is used for both observation and photography.

It is another object of this invention to provide a larynx stroboscope wherein the light emission used for real time light observation is suspended by camera shutter to increase the power of the flash discharge.

Yet another object of this invention is to provide for a larynx stroboscope wherein following the flash emission for photography the observation light is restored.

These and other objects of this invention will be described in greater detail in the drawings and the description of the preferred embodiments that follow.

DESCRIPTION OF THE PREFERRED EMBODIMENTS

Figure 1:
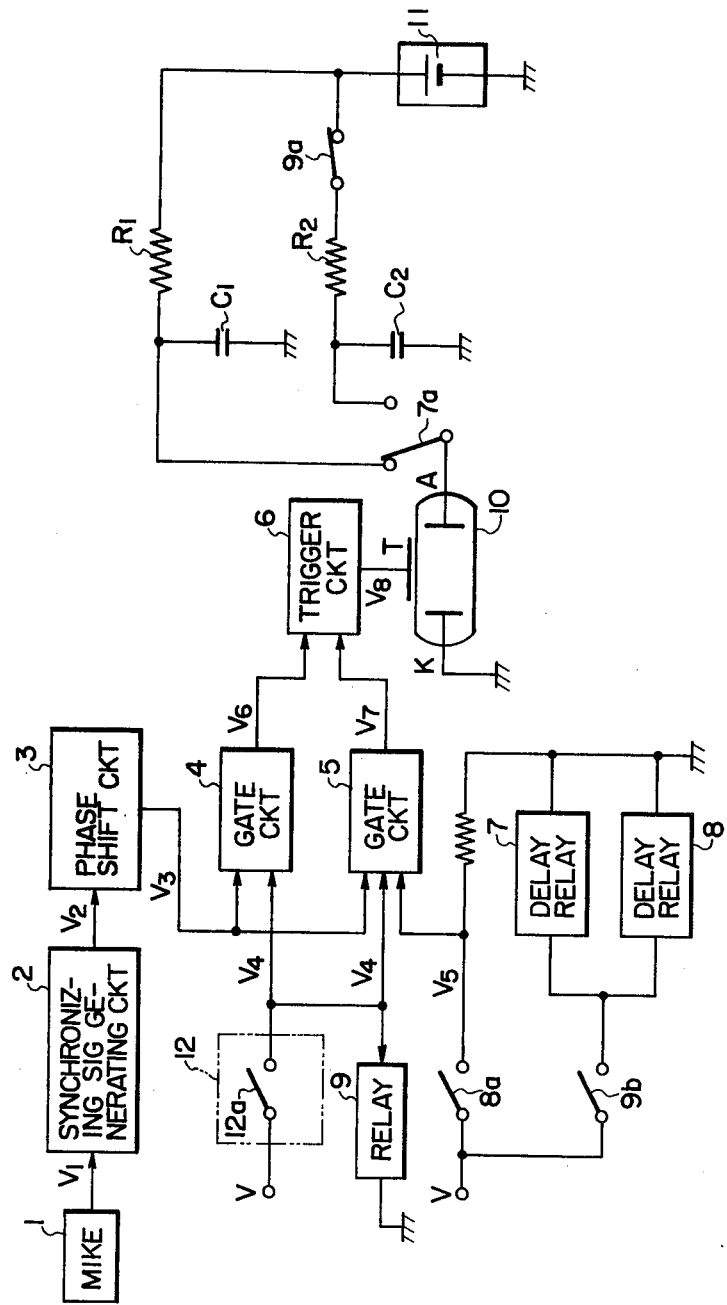
FIG. 1 is a block diagram showing one embodiment of this invention.

Referring now to FIG. 1 a block diagram showing one example of a larynx stroboscope device according to the invention is shown. A vocal cord vibration signal $V_1$ detected by a microphone 1 is applied to a synchronizing signal generating circuit 2, which produces an output pulse $V_2$ in synchronization with the fundamental wave of the signal $V_1$. The circuit 2 may be a Schmitt trigger circuit, and it may be configured as shown in co-pending application entitled "LARYNX STROBOSCOPE DEVICE", Ser. No. 960,544 filed on the same day as this invention. The pulse $V_2$ is applied to a phase shift circuit 3, which provides a pulse signal (the peak value being V) $V_3$ obtained by delaying the pulse $V_2$. A gate circuit 4 operates to raise its output $V_6$ to "V" only when the input signal $V_3$ is at "V" and an input signal $V_4$ is at "0". A gate circuit 5 operates to raise its output $V_7$ to "V" only when all of the input signals $V_3$, $V_4$ and $V_5$ are at "V".

In FIG. 1, a trigger circuit 6 produces an output high voltage trigger pulse $V_8$ when the signal $V_6$ or $V_7$ is raised to "V". These circuits can be readily obtained by using relays, transistors and integrated circuits as is well established in the art.

When photography is not carried out, the flash synchro contact 12a of a camera 12 is open and the signal $V_4$ is at "0". Accordingly, the output $V_7$ of the gate circuit 5 is at "0" irrespective of the signal $V_3$. On the other hand, the output $V_6$ of the gate circuit 4 is at "V" only when the signal $V_3$ is at "V". Accordingly, the signal $V_6$ is produced in synchronization with the signal $V_3$ and the high voltage trigger pulse $V_8$ is applied to the trigger terminal T of a flash discharge tube 10.

The flash discharge tube 10 is placed in excitement state (in which the impedance between the anode A and the cathode K is low) by the application of the trigger pulse $V_8$. Therefore, the charge in a charge-discharge capacitor $C_1$ will flow into the flash discharge tube 10 in a short time and as a result a light flash is emitted. Thereafter, the signals $V_3$, $V_6$ and $V_8$ are set to "0", and the state of the circuit is returned to its state obtained before the light emission.

Now, the case where photography is carried out will be described. In this situation, by the release operation of the camera 12, the flash synchro contact means 12a is closed, and the signal $V_4$ is raised to "V". In this operation, the output $V_6$ of the gate circuit 4 is set to "0" irrespective of the signal $V_3$. Since the flash synchro contact means 12a is closed, a relay 9 is operated to open its contact 9a, as a result of which supply of charging current to a charge-discharge capacitor $C_2$ from a high voltage generating circuit 11 is suspended. At the same time, another contact 9b is closed.

In FIG. 1, delay relays 7 and 8 having contacts 7a and 8a are operated $t_1$ and $t_2$ seconds after the closure of the contact means 9b, respectively. Accordingly, immediately after the flash synchro contact 12a is closed, the contact 8a is still open, and therefore the signal $V_5$ is at "0". Hence, the output $V_7$ of the gate circuit 5 is at "0" irrespective of the signal $V_3$, and the flash light emission of the flash discharge tube 10 is not carried out. The armature of the contact 7a is tripped over to the charge-discharge capacitor $C_2$ side by the delay relay 7 $t_1$ seconds after the contact 9b. Then, the delay relay 8 is operated $t_2$ seconds after the closure of the contact 9b to close the contact 8a. Therefore, the signal $V_5$ is raised to "V". The output $V_7$ of the gate circuit 5 is raised to "V" when the signal $V_3$ is raised to "V". Accordingly, when the signal $V_3$ is raised to "V" after the closure of the contact 8a, the high voltage trigger pulse $V_8$ is generated by the trigger circuit 6. This trigger pulse $V_8$ excites the flash discharge tube 10 and as the charges in the charge-discharge capacitor $C_2$ are delivered through the contact means 7a into the flash discharge tube 10 to permit the latter 10 to emit light flash.

The signals $V_3$, $V_7$ and $V_8$ are continuously generated in the form of pulses. However, since the contact 9a is open, the charge-discharge capacitor $C_2$ is not charged by the high voltage generating circuit 11. Therefore, light emission is not carried out by the flash discharge tube 10. When the contact 12a is opened after the completion of the photography operation, the contact 9a of the relay 9 is closed while the contact 9b is open. Therefore, the armature of the contact 7a of the delay relay 7 is tripped over to the charge-discharge capacitor $C_1$ side, and the contact 8a of the delay relay 8 is opened. As a result, the output $V_7$ of the gate circuit 5 is held at "0".

Conversely, the signal $V_4$ is set up to "0", and therefore the signals $V_6$ and $V_8$ are produced in synchronization with the signal $V_3$, and the state of the flash discharge 10 is automatically shifted to be ready for emitting light for real time observation. Since the contact 9a is closed, the charge-discharge capacitor $C_2$ is charged to be ready for the next photographing flash.

Figure 2:
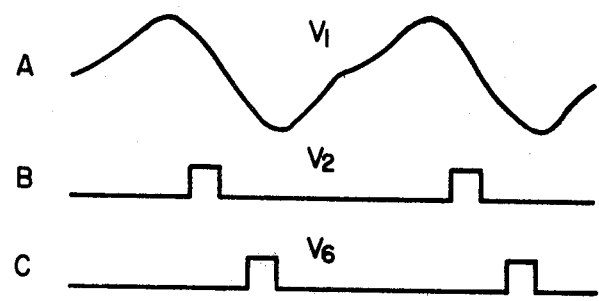
FIG. 2 is a time chart in the case where a photographing operation is not carried out.

FIG. 2 is a time chart in the case where the photography is not carried out. FIG. 2A indicates the vocal cord vibration signal $V_1$; FIG. 2B is the output $V_2$ of the synchronizing signal generating circuit; FIG. 2C is the output $V_6$ of the gate circuit 4.

Figure 3:
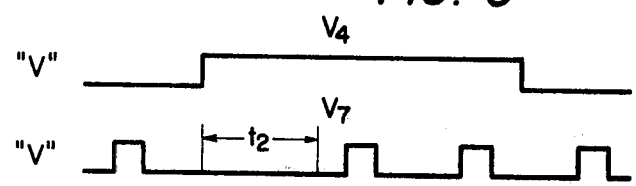
FIG. 3 is a time chart in the case where the photographing operation is carried out.

FIG. 3 is a time chart in the case where photography is carried out. The time chart shows that when the signal $V_4$ is raised to "V", the signal $V_7$ is maintained at "0" and is generated as an output pulse $t_2$ seconds after the signal $V_4$ is raised to "V".

In the above description, the anode terminal A of the flash discharge tube 10 is connected selectively to the charge-discharge capacitors $C_1$ and $C_2$ by the switching circuit. However, the same effect as that described above can be obtained by connecting the charge-discharge capacitor $C_1$ to the flash discharge tube 10 at all times in the following cases: (1) where the photographing flash light emission is sufficiently greater than the observing flash light emission even if the observing flash light emission is effectuated while the shutter is open, no difficulties will result; (2) where supply of charging current to the charge-discharge capacitor $C_1$ is stopped while the shutter is open and the flash light emission of the flash discharge tube 10 is not effected by the charge-discharge capacitor $C_1$; and (3) where the trigger pulse in the photography operation is stored, and the trigger pulses provided for the period of time which elapses from the occurrence of the trigger pulse stored until the photography operation is returned to the observing operation, are detected to be eliminated.

Figure 4:
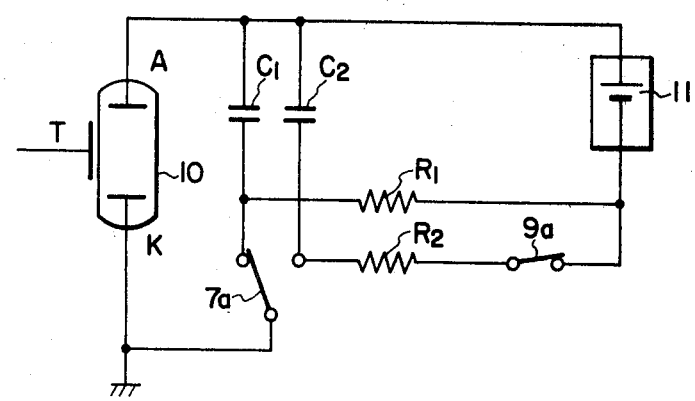
FIG. 4 is a circuit diagram showing one example of a circuit for switching the discharge paths of a flash discharge tube.

In the embodiment shown in FIG. 1, the charge-discharge capacitor switching contact 7a is provided on the side of the anode terminal A of the flash discharge tube 10. However, the same result can be obtained by providing the charge-discharge capacitor switching contact 7a on the side of the cathode K of the flash discharge tube so that the discharge paths of the flash discharge tube are switched on the side of the cathode K. This is shown in FIG. 4. In this connection, even if the cathode terminal of the flash discharge tube 10 remains connected to the observing charge-discharge capacitor $C_1$, the same effect can be obtained as described before.

The embodiment described above is designed so that in the case where the flash light emission is used for photography the anode or cathode terminal of the flash discharge tube is connected to the charge-discharge capacitor $C_2$ and after charging, the photographing charge-discharge capacitor $C_2$ is suspended. However, the same result can be obtained by modifying the embodiment in such a manner that charging of the photographing charge-discharge capacitor $C_2$ is suspended after the capacitor $C_2$ is connected to the anode or cathode terminal of the flash discharge tube.

In the embodiment shown in FIGS. 1 and 4, the continuous-discharge (the state where, although no trigger voltage is applied to the trigger terminal T of the flash discharge tube 10, discharge from the high voltage circuit 11 cannot be stopped) preventing contact 9a is provided in order that the charging time of the charge-discharge capacitor $C_2$ is shortened by decreasing the resistance $R_2$. However, in the case where it is possible to make the photographing flash light emission interval longer, the charging time of the charge-discharge capacitor $C_2$ can be made longer. In this case, the resistance $R_2$ may be increased so that the charging current of the charge-discharge capacitor $C_2$ is decreased to the extent that the flash discharge tube 10 causes no continuous discharge. Then, it is unnecessary to break the charging of the charge-discharge capacitor $C_2$ by means of the contact 9a, which leads to a reduction of the manufacturing cost of the device.

Preferably, the photography flash light emission is made only once while the shutter is open in order to obtain a clear photographing image. However, sometimes it is required to carry out the flash light emission a multiple number of times while the shutter is held open because of the intensity of flash light emitted by the flash discharge tube, the capacitance and dielectric strength of the charge-discharge capacitor, or the like. In this case, if the photography charge-discharge capacitor is charged immediately after the flash light emission, or if two photography charge-discharge capacitors or more are provided in such a manner that they can be switched over, then the photography flash light emission can occur a multiple number of times while the shutter is open.

The embodiment according to the invention uses relays and intergrated circuits; however, the relays may be readily replaced by thyristors, transistors and integrated circuits. Other modifications are also possible without departing from the essential scope of this invention.

As is apparent from the above description, an excellent larynx stroboscope device with which the image of vocal cords can be readily photographed at a desired time instant while observing the vocal cords being vibrated is provided according to the invention.

We claim:

1. In a larynx stroboscope adaptable for use with a camera for photographing a larynx the improvement comprising, means to generate a larynx vibration signal, a flash discharge tube having an anode and a cathode and selectively connected to a photographing charge discharge capacitor by the release operation of a camera, circuit means connected to said capacitor for precharging said capacitor during observation, means responsive to said release operation for disconnecting said capacitor from said circuit means, and for reconnecting said capacitor to said circuit means after the light emission of said flash discharge tube, whereby said capacitor is immediately ready for photographic operation upon said release operation, means to apply a trigger pulse to a trigger terminal of said flash discharge tube in synchronization with a vocal cord vibration signal, wherein said flash discharge tube emits light while the shutter of said camera is open, and after a photographing operation is complete, the functions of said flash discharge tube are automatically restored to a state of light emission for observation before the shutter release operation.

2. The larynx stroboscope of claim 1 wherein the anode of said flash discharge tube is connected to said charge-discharge capacitor.

3. The larynx stroboscope of claim 1 wherein the cathode of said flash discharge tube is connected to said charge-discharge capacitor.

4. The larynx strobscope of claim 1 wherein the means to generate a larynx vibration signal comprises, a sensor and a synchronizing signal generating circuit responsive to the output of the sensor.

5. The larynx stroboscope of claim 1 or 4 wherein the means to apply a trigger pulse comprises, means responsive to the shutter release operation of said camera to suspend charging of said discharge tube, and gate means responsive to said shutter release operation and as larynx vibration signal to generate a trigger signal and apply it to the trigger terminal of said flash discharge tube.

6. The larynx stroboscope of claim 5 further comprising a delay circuit coupled to said gate means to delay actuation of said trigger pulse for a predetermined time following release of said shutter release.

7. A method of using a larynx stroboscope capable of photographing the larynx comprising the steps of charging a photographing charge-discharge capacitor by means of a high voltage generating circuit, disconnecting said generating circuit from said photographing charge-discharge capacitor prior to the light emission of a flash discharge tube, connecting said flash discharge tube to said photographing charge-discharge capacitor by the release operation of a camera, applying a trigger pulse to a trigger terminal of said flash discharge tube in synchronization with a vocal cord vibration frequency so that said flash discharge tube emits light while the shutter of said camera is open, and following completion of the photographing operation restoring the observation function of the stroboscope to the state of operation before the shutter release operation.

8. The method of claim 7 further comprising the step of generating a second light emission from said flash discharge tube while said shutter is held open.

9. The method of claim 7 further comprising the step of charging said charge-discharge capacitor following completion of said photographing operation.

10. The method of claims 7, 8 or 9 further comprising the step of coupling a terminal of said flash discharge device to said charge-discharge capacitor prior to suspension of charging current to said capacitor.

11. The method of claims 7, 8 or 9 further comprising the step of coupling a terminal of said flash discharge device to said charge-discharge capacitor subsequent to suspension of charging current to said capacitor.

* * * * *